United States Patent [19]

Kiefer et al.

[11] Patent Number: 5,212,074

[45] Date of Patent: May 18, 1993

[54] GENETIC MATERIAL ENCODING NEW INSULIN-LIKE GROWTH FACTOR BINDING PROTEIN IGFBP-6

[75] Inventors: Michael C. Kiefer, Clayton; Frank R. Masiarz, San Francisco, both of Calif.

[73] Assignee: Chiron Corporation, Emeryville, Calif.

[21] Appl. No.: 576,629

[22] Filed: Aug. 31, 1990

Related U.S. Application Data

[62] Division of Ser. No. 574,613, Aug. 28, 1990, abandoned.

[51] Int. Cl.$^5$ .................... C12P 21/02; C07H 21/04; C12N 1/00
[52] U.S. Cl. ................... 435/69.6; 435/69.1; 435/252.3; 435/240.1; 435/243; 435/254; 536/23.5; 935/9; 935/11; 935/66; 530/395
[58] Field of Search ............ 514/44; 530/303, 399; 435/69.1, 70.1, 71.1, 252.3, 252.33, 255, 240.2, 69.5, 240.1, 240.2, 240.4, 254, 255, 243, 69.6; 935/13, 9; 800/2; 536/27

[56] References Cited

FOREIGN PATENT DOCUMENTS

| | | |
|---|---|---|
| 369943 | 5/1990 | European Pat. Off. . |
| WO89/08667 | 9/1989 | World Int. Prop. O. . |
| WO89/09268 | 10/1989 | World Int. Prop. O. . |
| WO89/09792 | 10/1989 | World Int. Prop. O. . |
| WO90/00569 | 1/1990 | World Int. Prop. O. . |

OTHER PUBLICATIONS

Povoa, et al., Isolation and Characterization of a Somatomedin–Binding Protein from Midterm Human Amniotic Fluid, Eur. J. Biochem, Jul. 1984, 144: 199–204.

Koistinen et al., Placental Protein 12 is a Decidual Protein that Binds Somatomedin and has an Identical N–Terminal Amino Acid Sequence ..., Endocrinology, 1986, 118:1375–1378.

Powell, et al., Method for Purification of an Insulin—Like Growth Factor-Binding Protein Produced by Human Hep G2 Hepatoma Cells, Journal of Chromatography, 420, 1987, 420:163.

Lee, et al., Insulin-Like Growth Factor (IGF) Binding Protein Complementary Deoxyribonucleic Acid from Human Hep G2 Hepatoma Cells..., Mol. Endocrinology, 1988, 2:404–411.

Brinkman, et al., Isolation and Characterization of cDNA Encoding the Low Molecular Weight Insulin—Like Growth Factor Binding Protein (IBP-1), EMBO Jrn., 1988, 7: 2417–2423.

(List continued on next page.)

*Primary Examiner*—Robert A. Wax
*Assistant Examiner*—Gabriele E. Bugaisky
*Attorney, Agent, or Firm*—Barbara G. McClung; Richard L. Neeley

[57] ABSTRACT

A purified binding protein selected from the group consisting of insulin-like growth factor binding protein having an amino acid sequence which is at least 85% homologous to the amino acid sequence of FIG. 1 and fragments thereof comprising at least 10 consecutive amino acids of the sequence that are capable of binding to an antibody specific for the protein or to an insulin-like growth factor is described. Recombinant DNA molecules encoding the binding proteins and subsequences thereof are also described along with recombinant microorganisms and cell lines containing the DNA molecules and methods for preparing the binding proteins by growing the recombinant hosts containing the relevant DNA molecules. Antibodies to the protein, identified as IGFBP-6, which are useful in various diagnostic applications, are also described.

11 Claims, 6 Drawing Sheets

OTHER PUBLICATIONS

Brewer, et al., Cloning, Characterization, and Expression of a Human Insulin-Like Growth Factor Binding Protein, Biochemical and Biophysical Research Com., 1986, 152:1289–1297.

Binkert, et al., Cloning, Sequence Analysis and Expression of a cDNA Encoding a Novel Insulin-Like Growth Growth Factor . . ., EMBO Journ., 1989, 8: 2497–2502.

Baxter, et al., Growth Hormone-Dependent Insulin-Like Growth Factor (IGF) Binding Protein from Human Plasma . . ., Biochemical and Biophysical Research Com. 1986, 139:1256–1261.

Wood, et al., Cloning and Expression of the Growth Hormone-Dependent Insulin-Like Growth Factor-Binding Protein, Molecular Endocrinology, 1988, 2:;1176–1185.

Mottola et al., Purification and Amino-Terminal Sequence of an Insulin-Like Growth Factor Binding Protein Secreted by Rat Liver . . ., Journ. of Biol. Chem., 261:11180–11188.

Lyons, et al., Characterization of Multiplication-Stimulating Activity (MSA) Carrier Protein, Mol. Cell. Endocrinol., 1986, 45:263–270.

Mohan, et al., Isolation of an Inhibitory Insulin-Like Growth Factor (IGF) Binding Binding Protein from Bone . . ., Proc. Natl. Acad. Sci., 1989, 86:8338–8342.

Zapf, et al., Isolation from Adult Human Serum of Four Insulin-Like Growth Factor . . ., Journal of Biological Chemistry, 1990, 265:14892–14898.

Shimasaki, et al., Molecular Cloning of the cDNAs Encoding a Novel Insulin-Like Growth Factor-Binding Protein from Rat and Human, Mol. Endocrinology, 1990, 4:1451–1458.

```
     AlaGluGlyCysLeuArgArgGluGlyGlnGluCysGlyValTyrThrProAsnCysAla
242  GCTGAGGGCTGTCTCAGGAGGAGGGGGCAGGAGTGCGGGGTCTACACCCCTAACTGCGCC
     CGACTCCCGACAGAGTCCTCCTCCCCCGTCCTCACGCCCCAGATGTGGGGATTGACGCGG

ProGlyLeuGlnCysHisProProLysAspAspGluAlaProLeuArgAlaLeuLeuLeu
302  CCAGGACTGCAGTGCCATCCGCCAAGGACGACGAGGCCCTTTGCGGGCGCTGCTCTC
     GGTCCTGACGTCACGGTAGGCGGGTTCCTGCTGCTCCGGGAAACGCCCCGACGACGAG

308 PSTI, 337 NARI, 361 XMA3,

GlyArgGlyArgCysLeuProAlaArgAlaAlaProAlaValAlaAlaGluAsnProLysGlu
362  GGCCGAGGCCGCTGCCTTCCGGCCCGCGCCGCTGCTGTTGCAGAGGAGAATCCTAAGGAG
     CCGGCTCCGGCGACGGAAGGCCGGGCGCGGCGACGACAAGCGTCTCCTCTTAGGATTCCTC

387 BSSH2, 413 MST2,

SerLysProGlnAlaGlyThrAlaArgProGlnAspValAlaAsnArgArgAspGlnArg
422  AGTAAACCCCAAGCAGGCACTGCCCGCCCACAGGATGTGAACCGCAGAGACCAACAGAGG
     TCATTTGGGGTTCGTCCGTGACGGGCGGGTGTCCTACACTTGGCGTCTCTGGTTGTCTCC

435 ALWN1

AsnProGlyThrSerThrProSerGlnProAsnSerAlaGlyValGlnAspThrGlu
482  AATCCAGGCACCTCTACCACGCCCAGCCAATTCTGCGGGTGTCCAAGACACTGAG
     TTAGGTCCGTGGAGATGGTGCGGGAGGTCGGGTTAAGACGCCCACAGGTTCTGTGACTC
```

```
     MetGlyProCysArgArgHisLeuAspSerValLeuGlnGlnLeuGlnThrGluValTyr
542  ATGGGCCCATGCCGTAGACATCTGGACTCAGTGCTGCAGCAACTCCAGACTGAGGTCTAC
     TACCCGGGTACGGCATCTGTAGACCTGAGTCACGACGTCGTTGAGGTCTGACTCCAGATG

544 APAI, 575 PSTI,

ArgGlyAlaGlnThrLeuTyrValProAsnCysAspHisArgGlyPheTyrArgLysArg
602  CGAGGGGCTCAAACACTCTACGTGCCCAATTGTGACCATCGAGGCTTCTACCGGAAGCGG
     GCTCCCCGAGTTTGTGAGATGCACGGGTTAACACTGGTAGCTCCGAAGATGGCCTTCGCC

GlnCysArgSerSerGlnGlyGlnArgArgGlyProCysTrpCysValAspArgMetGly
662  CAGTGCCGCTCCTCCCAGGGCCAGCGCCGAGGTCCCTGCTGGTGTGTGGATCGGATGGGC
     GTCACGGCGAGGAGGGTCCCGGTCGCGGCTCCAGGGACGACCACACACTAGCCTACCCG

LysSerLeuProGlySerProAspGlyAsnGlySerSerSerCysProThrGlySerSer
722  AAGTCCCTGCCAGGGTCTCCAGATGGCAATGGAAGCTCCTCCTGCCCCACTGGGAGTAGC
     TTCAGGGACGGTCCCAGAGGTCTACCTTACCGTTACCTTCGAGGAGGACGGGGTGACCCTCATCG
```

```
            Stop
      GlyOC SerTrpGlyIleGluGlyLysLeuGlnGlyGlyHisTrpLysGluHisGlyAlaValIle
782   GGCTAAAGCTGGGGGATAGAGAGGGCTGCAGGGCCACTGGAAGGAACATGGAAGCTGTCATC
      CCGATTTCGACCCCCTATCTCCCCGACGTCCCGGTGACCTTCCTGTACCTCGACAGTAG

806 PSTI,

ThrGlnLysThrGluAlaLeuAsnProProSerGlyProAlaProTrpAlaProHis
842   ACTCAACAAAAAACCGAGGCCCTCAATCCACCTTCAGGGCCCCATGGGCCCCTCAC
      TGAGTTGTTTTTTGGCTCCGGGAGTTAGGTGGAAGTCCCGGGGTACCCGGGGAGTG

884 BGLI, 887 NCOI, 891 APAI,

ArgTrpLeuArgValLeuValLeuAlaGlyValSerIleLysLeuCysLeuGlySer
902   CGCTGGTTGGAAAGAGTGTTGGTGTTGGCTGGGGTGTCAATAAAGCTGTGCTTGGGGTCA
      GCGACCAACCTTTCTCACAACCACACCGACCCCACAGTTATTTCGACACGAACCCCAGT
                                               ‾‾‾‾‾‾‾‾‾‾‾‾‾‾‾‾
                                                  polyA signal
      AsnLeuAM Ile
962   AA|CCTGTAGATCC
      TT|GGACATCTAGG
        | linker Translation shown starts at frame 2.

Comparison of Various Human IGFBP Amino Acid Sequences

FIG. 2B

GENETIC MATERIAL ENCODING NEW INSULIN-LIKE GROWTH FACTOR BINDING PROTEIN IGFBP-6

This application is a division of U.S. application Ser. No. 07/574,613, filed Aug. 28, 1990 abandoned.

INTRODUCTION

1. Field of the Invention

This invention relates to genetic engineering of naturally occurring proteins and to corresponding recombinant proteins, genes, and gene segments and more specifically to such proteins and genetic elements derived from an insulin-like growth factor-binding protein, to methods and compositions which employ the proteins and genetic elements, and to gene segments that are useful in diagnosis.

2. Background

Insulin-like growth factors (IGFs) are low molecular weight polypeptide hormones with structural homology to proinsulin. Two different IGFs are known, namely IGF-I and IGF-II, which are mitogenic in vitro for a wide variety of cells in tissue culture. Both IGFs stimulate in vitro the growth of various tissues and in particular they induce collagen synthesis. IGF-I mediates the growth promoting effect of growth hormone in chondrogenesis and bone formation and is therefore essential for normal growth of an individual. This is demonstrated by the fact that pygmies and toy poodles are deficient in IGF-I but have normal growth hormone level in their serum. IGF-II is believed to play a key role in fetal development and nerve growth.

In addition to their primary effect on skeletal tissue they also exhibit growth-stimulating functions on other tissues. Wound fibroblasts are known to produce IGFs which are effective in stimulating fibroblasts to grow and synthesize collagen, a structural protein normally required for wound healing. Vascularization of the wound tissue is also induced. Further, it has also been found that IGFs have an erythropoietin-like activity in that they induce hematopoiesis.

Recent studies have also demonstrated that IGFs produced by certain cancer cells, e.g. breast and kidney cancer cells, auto-stimulate the proliferation of cancer cells and the vascular and fibrous tissues required to support the growth of cancer tissues.

In addition to this, both IGFs show a spectrum of metabolic activities similar to those of insulin, in that they stimulate, in particular, the transport and metabolism of glucose. The biological effects of IGFs and insulin are mediated through their binding to specific receptors. In particular, both IGFs have the ability to bind to the insulin receptor with approximately 100-fold lower affinity than does insulin.

Both IGFs have a concentration in blood approximately a hundred-fold higher than that of insulin. Hypoglycemia is prevented by a regulatory mechanism which involves carrier proteins present in blood and able to form complexes with IGFs. Thus, IGFs circulate in the blood in the form of a complex which has no insulin-like activity. Through their association with carrier protein (hereinafter referred to as IGF-binding proteins or IGFBPs), binding of IGFs to cell surface receptors is inhibited. It has also been demonstrated that another function of the IGF-binding proteins is to increase the short half-life of IGFs, which are subjected to rapid proteolytic degradation when present in the free form in blood.

In accordance with the foregoing, IGFs may be useful in vitro to stimulate a) the growth of animals and humans with growth hormone deficiency, b) tissue regeneration, such as erythropoiesis and chondrogenesis, c) wound healing and d) the functions of various organs e.g. liver or kidney. As a result of their chondrogenesis stimulating activity, IGFs are of particularly suitable use for bone formation, e.g. in the treatment of osteoporosis. IGFs for use in the above-referred treatments are advantageously administered to a subject in association with at least one IGF-binding protein. Administration of this combination rather than IGF alone has beneficial effects including the prevention of hypoglycemia and possible mitogenic effects at injection sites and the prolongation of IGF half-life. Further, it has been found that binding proteins are also useful for potentiating the erythropoietin like-effect of IGF-I. The binding proteins may also be useful for targeting IGFs to specific tissues.

When administered alone, i.e., without any IGF, the binding proteins may also be therapeutically useful for blocking the adverse effects of IGFs, such as those which occur when IGFs are produced in excess, e.g. free IGFs secreted by certain cancer cells e.g. hormone-producing cancer cells such as breast or kidney cancer cells. IGF-binding-protein therapy may also prevent blindness as a secondary effect of diabetic proliferation retinopathy. Indeed it has been shown that IGFs may be one of the factors stimulating endothelial and fibroblast proliferation in diabetic retinopathy.

Another therapeutic use of IGFBPs is the control of excessive growth in IGF-binding-protein-deficient subjects, since it is very likely that high IGF levels combined with abnormally low levels of binding protein are responsible for excessive growth.

In recent years, three major species of IGF-binding proteins, different in size and other properties, have been detected in the serum of rodents and humans.

The first binding protein discovered, now called IGFBP-3, is a glycoprotein of approximately 150 kd and composed of several subunits. Its formation, in contrast to that of the second, smaller IGF-binding protein, is growth hormone dependent.

The second binding protein discovered, now called IGFBP-1, has a molecular weight of approximately 30–40 kd in the human and the rat. The human IGFBP-1 has already been purified from various sources including amniotic fluid (Povoa, G. et al., Eur. J. Biochem (1984) 144:199, (therefore also referred to as amniotic fluid binding protein), placenta (Koistenen, R. et al., Endocrinology (1986) 118 : 1375), and conditioned medium of hepatoma G2 cells (Powell, D. R. et al., J. Chromatogr. (1987) 420: 163). The first two binding proteins have been characterized by their amino acid contents and their N-terminal amino acid sequences, and found identical or at least very similar. The comparison of the amino acid sequences of the IGF-binding protein isolated from hepatoma G2 cells (Lee, Y. L. et al., Mol. Endocrinol. (1988) 2 (5): 404) and the IGF-binding protein cloned from a placenta cDNA library (Brinkman, A. et al., The EMBO Journal (1988) 7 (8): 2417) reveals 99% homology. Further, these two amino acid sequences shown with the IGF-binding protein as coded by a cDNA library a homology of 94% (Brewer, M. T. et al., Bioch. Biophys. Res. Com. (1988) 152(3): 1289).

In addition to the two major forms of IGF-binding proteins, several other IGF-binding proteins have been identified in different human tissue extracts and cell culture media by Western blotting techniques and affinity labelling with [$I^{125}$]-IGF. Their molecular weights range from 15 to 150 kd and some of these proteins appear to be generated by proteolytic degradation of the larger IGF-binding-proteins. In particular, a 53 kd IGF-binding protein which has been purified from human serum represents a subunit of the 150-kd IGFBP-3 (Baxter, R.C. Biochem Biophys. Res. Com. (1966 139(3):1256).

Another form of IGF-binding protein has also been found in the conditioned medium from rat BRL-3A cells, and has a molecular weight of 33–36 kd approximately. A partial amino-terminal protein sequence of the rat BRL-3A binding protein has been determined (Mottolla, C. et al., J. of Biol. Chem. (1986) 261:11180; Lyons, R. M. Smith. G. L., Mol. Cell. Endocrinol.(1986) 45:263). The 33% degree of homology shown by the rat and human terminal sequences is not high enough to allow the respective binding proteins to be considered as equivalents.

An additional IGFBP, now called IGFBP-2, which is related to the BRL-3A binding protein, has also been found and its amino acid sequence fully established. The amino acid sequence of IGFBP-2 is distinct from that of the previously known binding proteins.

The existence of a number of different IGF-binding proteins indicate that these proteins have different functions. Since it is possible to diagnose disease states and to modify in various different ways the biological activity of IGFs using the currently known binding proteins, there is significant interest in the discovery of additional IGF-binding proteins having different biological properties.

RELEVANT LITERATURE

1. Daughaday, W. H., and Rotwein, P. (1989) Endocrine Reviews 10, 68–91.
2. Nissley, S. P., and Rechler, M. M. (1984). In: Hormonal Proteins and Peptides (C. H. Li, ed.) p. 127–203. Academic Press, New York and London.
3. Cohen, K. L., and Nissley, S. P. (1976) Acta Endocr. (Kbh.) 83, 243–258.
4. Zapf, J., Hauri, Ch., Waldvogel, M. and Froesch, E. R. (1986) J. Clin. Invest. 77, 1768–1775.
5. Guler, H. P., Zapf, J., Schmid, Ch., and Froesch, E. R. (1989) Acta Endocr (Kbh.) 121, 753–758.
6. Zapf, J., Hauri, C., Waldvogel, M., Futo, E., Hasler, H., Binz, K., Guler, H. P.,Schmid, C., and Froesch, E. R. (1989) Proc. Natl. Acad. Sci. USA 86, 3813–3817.
7. Schmid, C., Zapf, J., and Froesch, E. R. (1989) FEBS Letters 244, 328–332.
8. Schmid, Ch, Ernst, M., Zapf, J., and Froesch, E. R. (1989) Biochem. Biophys. Res. Commun. 160, 788–794.
9. Elgin, R. G., Busby, W. H., and Clemmons, D. R. (1987) Proc. Natl. Acad. Sci. USA 84, 3254–3258.
10. De Mellow, J. S .M., and Baxter, R.C. (1988) Biochem. Biophys. Res. Commun. 156, 199–204.
11. Knauer, D. J., and Smith, G. L. (1980) Proc. Nat. Sci. USA 77, 7252–7256.
12. Zapf, J., Waldvogel, M., and Froesch, E. R. (1975) Arch. Biochem. Biophys. 168, 638–645.
13. Hintz, R. L., Liu, F., Rosenfeld, R. G. and Kemp, S. F. (1981) J. Clin. Endocrinol. Metab, 53:100–104.
14. Martin, J. L., and Baxter, R. C. (1981) J. Clin. Endocrinol. Metab. 61, 799–801.
15. Baxter, R. C., and Martin, J. L. (1989) Proc. Natl. Acad. Sci. USA 86, 6898–6902.
16. Wood, W. I., Cachianes, G., Henzel, W. J., Winslow, G. A., Spencer, S. A., Hellmiss, R., Martin, J. L., and Baxter, R. C. (1988) Molecular Endocrinology 2, 1176–1185.
17. Zapf, J., Schmid, Ch., Guler, H. P., Waldvogel, M., Hauri, Ch., Futo, E., Hossenlrpp, p., Binoux, M., and Froesch, E. R. 91990) J. Cin. Invest.; in press.
18. Martin, J. L., and Baxter, R. C. (1986) J. Biol. Chem. 261, 8754–8760.
19. Zapf, J., Born, W., Chang, J.-Y., James P., Froesch, E. R., and Fischer, J. A. (1988) Biochem. Biophys. Res. Comm. 156, 1187–1194.
20. Nilson, B. L., and Brown, L. R. (1984) Anal. Biochem. 141, 311–315.
21. Hossenlopp, P., Seurin, D., Segovia-Quinson, B., Hardouin, S., and Binoux, M. (1986) Anal. Biochem. 154, 138–143.
22. Zapf, J., Walter, H., and Froesch, E. R. (1981) J. Clin. Invest. 68, 1321–1330.
23. Matsudaira, P. (1987) J. Biol. Chem. 262, 10035–10038.
24. Yuen, S. W., Chui, A. H., Wilson, K. J., and Yuan, P. M. (1988) Applied Biosystems, User Bulletin No. 36, 1–17.
25. Hunkapiller, M. W., Hewick, R. M., Dreyer, W. J., and Hood, L. E. (1983) Methods in Enzymology 91, 399–413.
26. Friedman, M., Krull, L. G., and Cavins, J. F. (1980) J. Biol. Chem. 245, 3868–3871.
27. Chirgwin, J. M., Przbyla, A. E., MacDonald, R. J., and Rutter, W. J. (1979) Biochemistry 18, 5294–5299.
29. Aviv, H., and Leder, P. (1972) Proc. Natl. Acad. Sci. USA 69, 1408–1412.
30. Maniatis, T., Fritsch, E. F., and Sambrook, J. (1982) Molecular Cloning, a Laboratory Manual (Cold Spring Harbor Lab, Cold Spring Harbor, N.Y.).
31. Binkert, C., Landwehr, J., Mary, J. -L., Schwander, J., and Heinrich G. (1989) EMBO Journal 8, 2497–2502.
32. Margot, J. B., Binkert, C., Mary, J.-L., Landwehr, J., Heinrich, G., and Schwander, J. (1989) Molecular Endocrinology 3, 1053–1060.
33. Okayama, H., and Berg, P. (1983) Mol. and Cell. Biol. 3, 280–289.
34. Aruffo, A., and Seed, B. (1987) Proc. Natl. Acad. Sci. USA 84, 8573–8577.
35. Pfeiffer, B. H., and Zimmerman, S. B. (1983) Nucl. Acids Res. 11, 7853–7871.
36. Benton, W. D., and Davis, R. W. (1977) Science 196, 180–182.
37. Yanisch-Perron, C., Vieira, J., and Messing, J. (1985) Gene 33, 103–119.
38. Sanger, F., Nicklen, S., and Coulson, A. R. (1977) Proc. Natl. Acad. Sci USA 74, 5463–5467.
39. Barr, P. J., Tjhayer, R. M., Laybourn, P., Najarian, R. C., Seela, F., and Tolan, D. (1986) Biotechniques 4, 428–432.
40. Lehrach, H., Diamond, D., Wozney, J. M., and Boedtker, H. (1977) Biochemistry 16, 4743–4751.
41. Thomas, P. (1980) Proc. Natl. Acad. Sci. USA 77, 5201–5205.
42. Feinberg, A. P., and Vogelstein, B. (1984) Anal. Biochem. 137, 266–267.
43. Laron, Z. (1974) Isr. J. Med. Sci. 10, 1247–1253.

44. Ballard, J., Baxter, R. C., Binoux, M., Clemmons, D., Drop, S., Hall, K., Hintz, R. L., Rechler, M. M., Rutanen, E., and Schwander, J. J. (1989) Acta Endocr. (Kbh.) (Kbh.) 121, 751–752.
45. Roghani, M., Hossenlopp, P., Lepage, P., Balland, A., and Binoux, M. (1989) FEBS Letters 255, 253–258.
46. Martin, J. L., Willetts, K. E., and Baxter, R. C. (1990) J. Biol., Chem. 265, 4124–4130.
47. Ruoslahti, E., and Pierschbacher, M. D. (1987) Science 238, 491–497.
48. Obara, M., Chang, M. S., and Yamada, K. M. (1988) Cell 53, 649–657.
49. Mottola, C., MacDonald, R. G., Brackett, J. L., Mole, J. E., Anderson, J. K., and Czech, M. P. (1986) J. Biol. Chem. 261, 11180–11188.
50. Brown, A. L., Chiariotti, L., Orlowski, C. C., Mehlman, T., Burgess, W. H., Ackerman, E. J., Bruni, C. B., and Rechler, M. M. (1989) J. Biol. Chem. 264, 5148–5154.
51. Albiston, A. L. and A. C. Herington (1990) Biochem. Biophys. Res. Commun. 166, 892–897.
52. Wang, J. F., Hampton, B., Mehlman, T., Burgess, W. H., and Rechler, M. M. (1988) Biochem. Biophys. Res. Commun. 157, 718–726.
53. Huhtala, M. L., Koistinen, R., Palomaki, P., Partanen, P., Bohn, H., and Seppala, M. (1986) Biochem. Biophys. Res. Commun. 141, 263–270.
54. Lee, Y. L., Hintz, R. L., James, P. M., Lee, P. D. K., Shivley, J. E., and Powell, D. R. (1988) Molecular Endocrinology 2, 404–411.
55. Brewer, M. T, Stetler, G. L., Squires, Ch.H., Thompson, R. C., Busby, W. H., and Clemmons, D. R. (1988) Biochem. Biophys. Res. Comun. 152, 1289–1297.
56. Brinkman, A., Groffen, C., Kortleve, D. J., Van Kessel, A. G., and Drop, S. L. S. (1988) EMBO Journal 7, 2417–2423.
57. Julkunen, M., Koistinen, R., Aalto-Setala, M., Janne, O. A., and Kontula, K. (1988) FEBBS Letters 236, 295–302.
58. Luthman, H., Soderling-Barros, J., Persson, B., Engberg, C., Stern, I., Lake, M., Franzen, S.-A., Israelsson, M., Raden, B., Lindgren,B., Hjelmqvist, L., Enerb ck, S., Carlsson, P., Bjursell, G., Povoa, G., Hall, K., and J rnvall, H. (1989) Eur. J. Biochem. 180, 259–265.
59. Mohan, S., Bautista, C. M., Wergedal, J., and Baylink, D. J., (1989) Proc. Natl. Acad. Sci. USA 86, 8338–8342.
60. Szabo, L., Mottershead, D. G., Ballard, F. J., and Wallace, J. C. (1988) Biochem. Biophys. Res. Comm. 151, 207–214.

SUMMARY OF THE INVENTION

Accordingly, it is an object of the present invention to provide means for producing an IGF-binding protein by genetic engineering techniques, the binding protein having biological properties different from those of IGFBP-1, IGFBP-2, and IGFBP-3.

It is further an object of the present invention to provide recombinant DNA molecules capable of expressing the new IGF-binding protein in order that the binding protein will be more readily available.

These and other objects of the invention have been accomplished by providing genetic information encoding a binding protein selected from a group consisting of an insulin-like growth factor binding protein having an amino acid sequence which is at least 85% homologous to the amino acid sequence of FIG. 1 and fragments thereof comprising at least ten (10) consecutive amino acids of said sequence, wherein said purified binding protein is capable of binding to an antibody specific for said protein or to an insulin-like growth factor. Recombinant DNA molecules comprising a nucleic acid sequence encoding the new insulin-like growth factor binding protein and its fragments are also a part of the present invention along with recombinant microorganisms and cell lines capable of expressing the protein and antibodies that recognize the new binding protein.

DESCRIPTION OF THE DRAWINGS

FIGS. 1A–1D show the amino acid and nucleotide sequence of a clone encoding human IGFBP-6. An arrow shows the putative serine peptidase cleavage site.

FIGS. 2A and 2B compare the amino acid sequences of a human binding protein of the invention, human IGFBP-6, to the known sequences of the three human binding proteins discussed above and another new human binding protein, IGFBP-4. Areas of homology can be seen in these sequences. These areas of homology are of particular interest as they indicated areas from which DNA probes can be obtained that have a high probability of success in finding related molecules. Two such homologous areas are indicated by brackets, although other areas of homology are also present.

DESCRIPTION OF SPECIFIC EMBODIMENTS

Figure 1A:
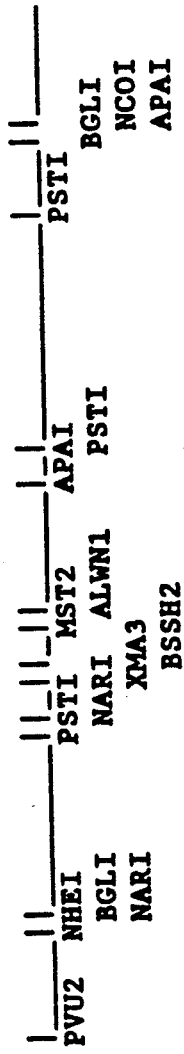

Novel compositions comprising generic sequences encoding IGFBP-6 and fragments derived therefrom are provided, together with recombinant proteins produced using the genetic sequences, and methods of using these compositions. The IGFBP-4 cDNA was initially isolated from a human osteosarcoma/λZAP cDNA library using a two-step procedure. First, small fragments of the cDNAs encoding amino acids 7 to 22 of IGFBP-6 were amplified from osteosarcoma cDNA by the polymerase chain reaction, gel purified, and sequenced. Second, perfect match-oligonucleotides were synthesized, based on the IGFBP-6 nucleotide sequence between the PCR primers, and were used as probes to isolate cDNA clones. IGFBP-6 cDNA clones showing the largest DNA insert size by agarose gel electrophoresis were sequenced. The nucleotide and encoded amino acid sequences of IGFBP-6 are shown in FIG. 1.

Standard abbreviations for nucleotides and amino acids are used in the figures and elsewhere in this specification.

A number of terms used in the art of genetic engineering and protein chemistry are used herein with the following defined meanings.

Two nucleic acid fragments are "homologous" if they are capable of hybridizing to one another under hybridization conditions described in Maniatis et al., op. cit., pp. 320–323. However, by using the following wash conditions—2×SCC, 0.1% SDS, room temperature twice, 30 minutes each; then 2×SCC, 0.1% SDS, 50° C. once, 30 minutes; then 2×SCC, room temperature twice, 10 minutes each—homologous sequences can be identified that contain at most about 25–30% basepair mismatches. More preferably, homologous nucleic acid strands contain 15–25% basepair mismatches, even more preferably 5–15% basepair mismatches. These degrees of homology can be selected by using more stringent wash conditions for identification of clones from gene libraries (or other sources of genetic material), as is well known in the art.

A DNA fragment is "derived from" an IGFBP-6-encoding DNA sequence if it has the same or substantially the same basepair sequence as a region of the coding sequence for the entire IGFBP-6 molecule.

Substantially the same means, when referring to biological activities, that the activities are of the same type although they may differ in degree. When referring to amino acid sequences, substantially the same means that the molecules in question have similar biological properties and preferably have at least 85% homology in amino acid sequences. More preferably, the amino acid sequences are at least 90% identical. In other uses, substantially the same has its ordinary English language meaning.

A protein is "derived from" an IGFBP-6 molecule if it has the same or substantially the same amino acid sequence as a region of the IGFBP-6 molecule.

IGFBP-6, both glycosylated and unglycosylated, or polypeptide derivatives thereof, may be used for producing antibodies, either nonoclonal or polyclonal, specific to IGFBP-6. By polypeptide derivatives is meant polypeptides differing in length from natural IGFBP-6 and containing five or more amino acids from IGFBP-6 in the same primary order as found in IGFBP-6 as obtained from a natural source. Polypeptide molecules having substantially the same amino acid sequence as IGFBP-6 but possessing minor amino acid substitutions that do not substantially affect the ability of the IGFBP-6 polypeptide derivatives to interact with IGFBP-6-specific molecules, such as antibodies and IGF molecules, particularly IGF-I and especially IGF-II, are within the definition of IGFBP-6. Derivatives include glycosylated forms, aggregative conjugates with other IGF-BP's molecules and covalent conjugates with unrelated chemical moieties. Covalent derivatives are prepared by linkage of functionalities to groups which are found in the IGF-BPs amino acid chain or at the N- or C-terminal residue by means known in the art.

Experiments with N-glycanase suggest that IGFBP-6 is not glycosylated; i.e., the mobility of the binding protein on gels does not change after digestion with N-glycanase. However, the encoded protein contains an N-glycosylation sits, and the protein therefore can be glycosylated under appropriate circumstances. Accordingly, the native molecule may contain a sugar that is buried in the molecule and is therefore inaccessable to glycanases. This is thought to be the case with a sugar chain on the IGFBP-3 molecule. A possible indication of glycosylation of the IGFBP-6 molecule is obtained from its molecular weight. The predicted molecular weight of IGFBP-6 (from the cDNA) is less than that obtained from gel mobility. However, experiments have not been able to detect sugar molecules.

IGFBP-6-specific molecules include polypeptides such as antibodies that are specific for the IGFBP-6 polypeptide containing the naturally occurring IGFBP-6 amino acid sequence. By "specific binding polypeptide" is intended polypeptides that bind with IGFBP-6 and its derivatives and which have a measurably higher binding affinity for the target polypeptide, i.e., IGFBP-6 and polypeptide derivatives of IGFBP-6, than for other polypeptides tested for binding. Higher affinity by a factor of 10 is preferred, more preferably a factor of 100. Binding affinity for antibodies refers to a single binding event (i.e., monovalent binding of an antibody molecule). Specific binding by antibodies also means that binding takes place at the normal binding site of the molecule's antibody (at the end of the arms in the variable region).

As discussed above, minor amino acid variations from the natural amino acid sequence of IGFBP-6 are contemplated as being encompassed by the term IGFBP-6; in particular, conservative amino acid replacements are contemplated. Conservative replacements are those that take place within a family of amino acids that are related in their side chains. Genetically encoded amino acids are generally divided into four families: (1) acidic=aspartate, glutamate; (2) basic=lysing, arginine, histidine; (3) non-polar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding properties of the resultinq molecule, especially if the replacement does not involve an amino acid at a binding site involved in the interaction of IGFBP-6 or its derivatives with an IGF molecule. Whether an amino acid change results in a functional peptide can readily be determined by assaying the specific binding properties of the IGFBP-6 polypeptide derivative. A binding assay is described in detail below.

Antibodies specific for IGFBP-6 are produced by immunizing an appropriate vertebrate host, e.g., rabbit, with purified IGFBP-6 or polypeptide derivatives of IGFBP-6, by themselves or in conjunction with a conventional adjuvant. Usually, two or more immunizations will be involved, and blood or spleen will be harvested a few days after the last injection. For polyclonal antisera, the immunoglobulins can be precipitated, isolated and purified by a variety of standard techniques, including affinity purification using IGFBP-6 attached to a solid surface, such as a gel or beads in an affinity column. For monoclonal antibodies, the splenocytes normally will be fused with an immortalized lymphocyte, e.g., a myeloid cell line, under selective conditions for hybridoma formation. The hybridomas can then be cloned under limiting dilution conditions and their supernatants screened for antibodies having the desired specificity. Techniques for producing antibodies are well known in the literature and are exemplified by the publication *Antibodies: A Laboratory Manual* (1988) eds. Harlow and Lane, Cold Spring Harbor Laboratories Press, and U.S. Pat. Nos. 4,381,292, 4,451,570, and 4,618,577.

IGFBP-6 can be readily purified from blood and its components, such as serum and plasma and from cells genetically modified to produce IGFBP-6 or polypeptide derivatives thereof, by affinity chromatography using a monoclonal antibody specific for IGFBP-6. In addition to the use of antibody affinity chromatography, IGFBP-6 and polypeptide derivatives thereof can be purified by a variety of other widely known protein purification techniques (either alone or in combination) including immunoprecipitation, gel filtration, ion exchange chromatography, chromatofocusing, isoelectric focusing, selective precipitation, electrophoresis, and the like. Fractions isolated during purification procedures can be analyzed for the presence of IGFBP-6 or polypeptide derivatives of IGFBP-6 by immunoassays employing IGFBP-6-specific antibodies or IGFBP-6-specific bioassays. Detailed examples are provided below.

Isolation of nucleotide sequences encoding IGFBP-6 involves creation of either a ganomic library prepared from cells encoding IGFBP-6 or preparation of a cDNA library from RNA isolated from calls expressing IGFBP-6. It will generally be preferable to create a cDNA library for isolation of IGFBP-6 coding nucleotide sequences so as to avoid any possible problems arising from attempts to determine intron/exon borders. Genetic libraries can be made in either eukaryotic or prokaryotic host cells. Widely available cloning vectors such as plasmids, cosmids, phage, YACs and the like can be used to generate genetic libraries suitable for the isolation of nucleotide sequences encoding IGFBP-6 or portions thereof.

Useful methods for screening genetic libraries for the presence of IGFBP-6 nucleotide sequences include the preparation of oligonucleotide probes based on the N-terminus amino acid sequence information from purified IGFBP-6 or purified internal fragments of purified IGFBP-6. By employing the standard triplet genetic code, oligonucleotide sequences of about 17 base pairs or longer can be prepared by conventional in vitro synthesis techniques so as to correspond to portions of IGFBP-6 for which the amino acid sequence has been determined by N-terminus analysis. The resultant nucleic acid sequences can be subsequently labeled with radionuclides, enzymes, biotin, fluorescers, or the like, and used as probes for screening genetic libraries.

Additional methods of interest for isolating IGFBP-6-encoding nucleic acid sequence: include screening genetic libraries for the expression of IGFBP-6 or fragments thereof by means of IGFBP-6-specific antibodies, either polyclonal or monoclonal. A particularly preferred technique involves the use of degenerate primers based on partial amino acid sequences of purified IGFBP-6 or on sequences from known related molecules and the polymerase chain reaction (PCR) to amplify gene segments between the primers. The gene can then be isolated using a specific hybridization probe based on the amplified gene segment, which is then analyzed for appropriate expression of protein. A detailed description of this preferred technique is set forth in the examples that follow.

Nucleotide sequences encoding IGFBP-6 can be obtained from recombinant DNA molecules recovered from IGFBP-6 genetic library isolates. The nucleotide sequence encoding IGFBP-6 can be obtained by sequencing the non-vector nucleotide sequences of these recombinant molecules. Nucleotide sequence information can be obtained by employing widely used DNA sequencing protocols, such as Maxim and Gilbert sequencing, dideoxy nucleotide sequencing, and the like. Examples of suitable nucleotide sequencing protocols can be found in Berger and Kimmel, *Methods in Enzymology Vol. 152, Guide to Molecular Cloning Techniques*, (1987) Academic Press. Nucleotide sequence information from several recombinant DNA isolates, including isolates from both cDNA and genomic libraries, may be combined so as to provide the entire amino acid coding sequence of IGFBP-6 as well as the nucleotide sequences of introns within the IGFBP-6 gene, upstream nucleotide sequences, and downstream nucleotide sequences.

Nucleotide sequences obtained from sequencing IGFBP-6 specific genetic library isolates are subjected to analysis in order to identify regions of interest in the IGFBP-6 gene. These regions of interest include open reading frames, introns, promoter sequences, termination sequences, and the like. Analysis of nucleotide sequence information is preferably performed by computer. Software suitable for analyzing nucleotide sequences for regions of interest is commercially available and lncludes, for example, DNASIS ™ (LKB). It is also of interest to use amino acid sequence information obtained from the N-terminus sequencing of purified IGFBP-6 when analyzing IGFBP-6 nucleotide sequence information so as to improve the accuracy of the nucleotide sequence analysis.

Isolated nucleotide sequences encoding IGFBP-6 can be used to produce purified IGFBP-6 or fragments thereof by either recombinant DNA methodology or by in vitro polypeptide synthesis techniques. By "purified" and "isolated" is meant, when referring to a polypeptide or nucleotide sequence, that the indicated molecule is present in the substantial absence of other biological macromolecules of the same type. The term "purified" as used herein preferably means at least 95% by weight, more preferably at least 99% by weight, and most preferably at least 99.8% by weight, of biological macromolecules of the same type present (but water, buffers, and other small molecules, especially molecules having a molecular weight of less than 1000, can be present).

A significant advantage of producing IGFBP-6 by recombinant DNA techniques rather than by isolating IGFBP-6 from natural sources is that equivalent quantities of IGFBP-6 can be produced by using less starting material than would be required for isolating the binding protein from a natural source. Producing IGFBP-6 by recombinant techniques also permits IGFBP-6 to be isolated in the absence of some molecules normally present in cells that naturally produce IGFBP-6. Indeed, IGFBP compositions entirely free of any trace of human protein contaminants can readily be produced since the only human protein produced by the recombinant nonhuman host is the recombinant IGFBP. Potential viral agents from natural sources are also avoided. It is also apparent that recombinant DNA techniques can be used to produce IGFBP-6 polypeptide derivatives that are not found in nature, such as the variations described above.

IGFBP-6 and polypeptide derivatives of IGFBP-6 can be expressed by recombinant techniques when a DNA. sequence encoding the relevant molecule is functionally inserted into a vector. By "functionally inserted" is meant in proper reading frame and orientation, as is well understood by those skilled in the art. When producing a genetic construction containing a complete IGFBP-6 reading frame, the preferred starting material is a cDNA library isolate encoding IGFBP-6 rather than a genomic library isolate. Typically, the IGFBP-6 gene will be inserted downstream from a promoter and will be followed by a stop codon, although production as a hybrid protein followed by cleavage may be used, if desired. In general, host-cell-specific sequences improving the production yield of IGFBP-6 and IGFBP-6 polypeptide derivatives will be used and appropriate control sequences will be added to the expression vector, such as enhancer sequences, polyadenylation sequences, and ribosome binding sites.

Once the appropriate coding sequence is isolated, it can be expressed in a variety of different expression systems.

MAMMALIAN EXPRESSION SYSTEMS

A mammalian promoter is any DNA sequence capable of binding mammalian RNA polymerase and initiating the downstream (3') transcription of a coding sequence (e.g. structural gene) into mRNA. A promoter will have a transcription initiating region, which is usually placed proximal to the 5' end of the coding sequence, and a TATA box, usually located 25–30 base pairs (bp) upstream of the transcription initiation site. The TATA box is thought to direct RNA polymerase II to begin RNA synthesis at the correct site. A mammalian promoter will also contain an upstream promoter element, typically located within 100 to 200 bp upstream of the TATA box. An upstream promoter element determines the rate at which transcription is initiated and can act in either orientation [Sambrook et al. (1989) "Expression of Cloned Genes in Mammalian Cells." In *Molecular Cloning: A Laboratory Manual, 2nd ed.*]

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter In addition, sequences derived from non-viral genes, such as the murine metallotheionein gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will typically increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter [Maniatis et al. (1987) *Science* 236:1237; Alberts et al. (1989) *Molecular Biology of the Cell*, 2nd ed.]. Enhancer elements derived from viruses may be particularly useful, because they typically have a broader host range. Examples include the SV40 early gene enhancer [Dijkema et al (1985) *EMBO J.* 4:761] and the enhancer/promoters derived from the long terminal repeat (LTR) of the Rous Sarcoma Virus [Gorman et al. (1982b) *Proc. Natl. Acad. Sci.* 79:6777] and from human cytomegalovirus Boshart et al. (1985) *Cell* 41:521]. Additionally, some enhancers are regulatable and become active only in the presence of an inducer, such as a hormone or metal ion [Sassone-Corsi and Borelli (1986) *Trends Genet.* 2:215; Maniatis et al. (1987) *Science* 236:1237].

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment typically encodes a signal peptide comprised of hydrophobic amino acids which direct the secretion of the protein from the cell. The adenovirus triparite leader is an example of a leader sequence that provides for secretion of a foreign protein in mammalian cells.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific posttranscriptional cleavage and polyadenylation [Birnstiel et al. (1985) *Cell* 41:349; Proudfoot and Whitelaw (1988) "Termination and 3' end processing of eukaryotic RNA. In *Transcription and Splicing* (ed. B. D. Hames and D. M. Glover); Proudfoot (1989) *Trends Biochem. Sci.* 14:105]. These sequences direct the transcription of an mRNA which can be translated into the polypeptide encoded by the DNA. Examples of transcription terminater/polyadenylation signals include those derived from SV40 [Sambrook et al (1989) "Expression of cloned genes in cultured mammalian cells." In *Molecular Cloning: A Laboratory Manual*].

Some genes may be expressed more efficiently when introns (also called intervening sequences) are present. Several cDNAs, however, have been efficiently expressed from vectors that lack splicing signals (also called splice donor and acceptor sites) [see e.g., Gothing and Sambrook (1981) *Nature* 293:620]. Introns are intervening noncoding sequences within a coding sequence that contain splice donor and acceptor sites. They are removed by a process called "splicing," following polyadenylation of the primary transcript [Nevins (1983) *Annu. Rev. Biochem.* 52:441; Green (1986) *Annu. Rev. Genet.* 20:671; Padgett et al. (1986) *Annu. Rev. Biochem.* 55:1119; Krainer and Maniatis (1988) "RNA splicing." In *Transcription and Splicing* (ed. B. D. Hames and D. M. Glover)].

Typically, the above described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (e.g., plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40 [Gluzman (1981) *Cell* 23:175] or polyomavirus, replicate to extremely high copy number in the presence of the appropriate viral T antigen. Additional examples of mammalian replicons include those derived from bovine papillomavirus and Epstein-Barr virus. Additionally, the replicon may have two replication systems, thus allowing it to be maintained, for example, in mammalian cells for expression and in a procaryotic host for cloning and amplification. Examples of such mammalian-bacteria shuttle vectors include pMT2 [Kaufman et al. (1989) Mol. Cell. Biol. 9:946 and pHEBO [Shimizu et al. (1986) Mol. Cell. Biol. 6:1074].

BACULOVIRUS EXPRESSION SYSTEMS

A baculovirus promoter is any DNA sequence capable of binding a baculovirus RNA polymerase and initiating the downstream (3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A baculovirus promoter may also have a second domain called an enhancer, which, if present, is usually distal to the structural gene. Expression may be either regulated or constitutive.

Sequences encoding genes abundantly transcribed at late times in the infection cycle provide particularly useful promoter sequences. Examples include sequences derived from the polyhedrin [Friesen et al. (1986) "The Regulation of Baculovirus Gene Expression," in: *The Molecular Biology of Baculoviruses* (ed. Walter Doerfler); E.P.O. Pub. Nos. 127,839 and 155,476]and p10 [Vlak et al. (1988) *J. Gen. Virol.* 69:765] genes.

A DNA molecule may be expressed intracellularly. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative to direct expression. Typically, a DNA sequence encoding the N-terminal portion of an endogenous yeast protein, or other stable protein, is fused to the 5' end of heterologous coding sequences. Upon expression, this construct will provide a fusion of the two amino acid sequences. For example, the N-terminus of the polyhedrin gene may be linked at the 5' terminus of a foreign gene and expressed in yeast. The DNA sequence at the junction of the two amino acid sequences may or may not encode a cleavable site. See e.g., Luckow et al (1988) *Bio/technology* 6:47.

Alternatively, foreign proteins can also be secreted from the cell by creating chimaric DNA molecules that encode a fusion protein comprised of a leader sequence fragment that provides for secretion of the foreign protein in insects. The leader sequence fragment typically encodes a signal peptide comprised of hydrophobic amino acids which direct the secretion of the protein from the cell.

DNA encoding suitable signal sequences can be derived from genes for secreted insect or baculovirus proteins, such as the baculovirus polyhedrin gene [Carbonell et al. (1988) *Gene* 73:409]. Alternatively, leaders of non-baculovirus origin, such as those derived from genes encoding human alphainterferon [Maeda et al. (1985) *Nature* 315:592], human gastrin-releasing peptide [Lebacq-Verheyden et al. (1988) *Molec. Cell. Biol.* 8:3129], human IL-2 [Smith et al. (1985) *Proc. Natl. Acad. Sci. USA* 82:8404], mouse IL-3 [Miyajima et al. (1987) *Gene* 58:273], and human glucocerebrosidase [Martin et al. (1988) *DNA* 7:99] also provide for secretion in insects.

Typically, transcription termination sequences recognized by insects are regulatory regions located 3' to the translation stop codon, and thus together with the promoter flank the coding sequence. These sequences direct the transcription of an mRNA which can be translated into the polypeptide encoded by the DNA. Examples include transcription termination sequences derived from the polyhedrin gene Miller et al. (1988) *Ann. Rev. Microbiol.* 42:177].

Prior to insertion of the foreign gene into the baculovirus genome, the above described components, comprising a promoter, leader (if desired), coding sequence of interest, and transcription termination sequence, are typically put together into an intermediate transplacement construct. Intermediate transplacement constructions are often maintained in a replicon, such as an extrachromosomal element (e.g., plasmids) capable of stable maintenance in a host, such as bacteria. The replicon will have a replication system, thus allowing it to be maintained in a prokaryotic host for cloning and amplification. The promoter and transcription termination sequence of the construct will typically comprise a 2.5 kb section of the baculovirus genome for integration of the foreign gene into the baculovirus genome by double crossover recombination events, producing a baculovirus expression vector [Miller et al. (1989) *Bloessays* 4:91]. The baculovirus expression vector is typically packaged into an infectious recombinant baculovirus.

When using baculovirus expression vectors, selectable markers, such as antibiotic resistence genes, are generally not used. Selection is typically by visual inspection for occlusion bodies. Examples are given elsewhere in this specification of the use of selectable markers.

Recombinant baculovirus expression vectors have been developed for infection into several insect cells. For example, recombinant baculoviruses have been developed for inter alia: *Aedes aegypti, Autographa californica, Bombyx mor, Drosophila melanogaster, Heliothis zea, Spodoptera frugiperda,* and *Trichoplusia ni* [P.C.T. WO 89/046699; Carbonell et al. (1985) *J. Virol.* 56:153: Smith et al. (1983) *Mol. Cell. Biol.* 3:2156; Wright (1986) *Nature* 321:718; See generally, Fraser et al. (1989) *In Vitro Cell. Dev. Biol.* 25:225].

Methods of introducing exogenous DNA into insect hosts are well-known in the art, and typically include either the transfection of host insect cells with DNA or the infection of insect cells or live insects, usually larvae, with virus. Transfection procedures are based on the calcium phosphate procedure originally developed for mammalian cells [Graham et al. (1973) Virology 52:456]. DNA transfection and viral infection proceedures usually vary with the insect genus to be transformed See e.g. Autograph [Carstens et al. (1980) *Virology* 101:311], *Heliothis (virescens)* [P.C.T. Pub. No. WO88/02030], Spodoptera [Kang (1988) "Baculovirus Vectors for Expression of Foreign Genes," in: *Advances in Virus Research,* vol. 35].

BACTERIAL EXPRESSION SYSTEMS

A bacterial promoter is any DNA sequence capable of binding bacterial RNA polymerase and initiating the downstream (3') transcription of a coding sequence (e.g. structural gene) into mRNA. A promoter will have a transcription initlation region which is usually placed proximal to the 5' end of the coding sequence. This transcription initiation region typically includes an RNA polymerase binding site and a transcription initiation site A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al. (1984) *Annu. Rev. Genet.* 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al. (1977) *Nature* 198:1056], and maltose. Additional examples include promoter sequences derived from biosynthetic enzymes such as tryptophan (trp) [Goeddel et al. (1980) *Nuc. Acids Res.* 8:4057; Yelverton et al. (1981) *Nucl. Acids Res.* 9:731; U.S. Pat. No. 4,738,921; E.P.O. Pub. Nos. 36,776 and 121,775]. The γ-lactamase (bla) promoter system [Weissmann (1981) "The cloning of interferon and other mistakes." In Interferon 3 (ed. I. Gresser)], bacteriophage lambda PL [Shimatake et al. (1981) *Nature* 292:128] and T5 [U.S. Pat. No. 4,689,406]promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433]. For example, the tac promoter is a hybrid trp-lac promoter comprised of both trp promoter and lac operon sequences that is regulated by the lac repressor [Amann et al. (1983) *Gene* 25:167; de Boer et al. (1983) *Proc. Natl. Acad. Sci.* 80:21]. Furthermore, a bacterial promoter can include naturally occurring promoters of non-bacterial origin that gave the ability to bind bacterial RNA polymerasa and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al. (1986) *J. Mol. Biol.* 89:113; Tabor et al. (1985) *Proc Natl Acad. Sci.* 82:1074]. In addition, a hybrid promoter can also be comprised of a bacteriophage promoter and an *E. coli* operator region (E.P.O. Pub. No. 267,851).

In addition to a functioning promoter sequence, an efficient ribosome binding site is also useful for the expression of foreign genes in prokaryotes In *E. coli*, the ribosome binding site is called the Shine-Dalgarno (SD) sequence and includes an initiation codon (ATG) and a sequence 3-9 nucleotides in length located 3-11 nucleotides upstream of the initiation codon [Shine et al. (1975) *Nature* 254:34]. The SD sequence is thought to promote binding of mRNA to the ribosome by the pairing of bases between the SD sequence and the 3' and of *E. coli* 16S rRNA [Steitz et al. (1979) "Genetic signals and nucleotide sequences in messenger RNA." In *Biological Regulation and Development: Gene Expression* (ed. R. F. Goldberger)]. To express eukaryotic genes and prokaryotic genes with weak ribosome-binding site Sambrook et al. (1989) "Expression of cloned genes in *Escherichia coli*." In *Molecular Cloning: A Laboratory Manual*].

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (E.P.O. Pub. No. 219,237).

Fusion proteins provide an alternative to direct expression. Typically, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene [Nagai et al. (1984) *Nature* 309:810]. Fusion proteins can also be made with sequences from the lacZ [Jia et al. (1987) *Gene* 60:197], trpE [Allen et al. (1987) *J. Biotechnol.* 5:93; Makoff et al. (1989) *J. Gen. Microbiol.* 135:11], and Chey [E.P.O. Pub. No. 324,647]genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g. ubiquitin specific processing-protease) to cleave the ubiquitin from the foreign protein. Through this method, native foreign protein can be isolated [Miller et al. (1989) *Bio/Technology* 7:698].

Alternatively, foreign proteins can also be secreted from the cell by creating chimaric DNA molecules that encode a fusion protein comprised of a signal peptide sequence fragment that provides for secretion of the foreign protein in bacteria [U.S. Pat. No. 4,336,336]. The signal sequence fragment typically encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA) [Masui et al. (1983), in: *Experimental Manipulation of Gene Expression;* Ghrayeb et al. (1984) *EMBO J.* 3:2437]and the *E. coli* alkaline phosphatase signal sequence (phoA) [Oka et al. (1985) *Proc. Natl. Acad. Sci.* 82:7212]. As an additional example, the signal sequence of the alpha-amylase gene from various Bacillus strains can be used to secrete heterologous proteins from *B. subtilis* [Palva et al. (1982) *Proc. Natl. Acad. Sci. USA* 79:5582; E.P.O. Pub. No. 244,042].

Typically, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Typically, the above described components, comprising a promoter, signal sequence if desired), coding sequence of interest, and transcription termination sequence, are put together into expression constructs. Expression constructs are often maintained in a replicon, such as an extrachromosomal element (e.g., plasmids) capable of stalled maintenance in a host, such as bacteria. The replicon will have a replication system, thus allowing it to be maintained in a procaryotic host either for expression or for cloning and amplification In addition, a replicon, may be either a high or low copy number plasmid. A high copy number plasmid will generally have a copy number ranging from about 5 to about 230, and typically about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors typically contain at least one sequence homologous to the bacterial chromosome that allows the vector to integrate. Integrations appear to result from recombinations between homologous DNA in the vector and the bacterial chromosome. For example, integrating vectors constructed with DNA from various Bacillus strains integrate into the Bacillus chromosome (E.P.O. Pub. No. 127,328). Integrating vectors may also be comprised of bacteriophage or transposon sequences.

Typically, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al. (1978) *Annu. Rev. Microbiol* 32:469]. Selectable markers may also include biosynthetic genes, such as those in the histidine, tryptophan, and leucine biosynthetic pathways.

Alternatively, some of the above described components can be put together in transformation vectors. Transformation vectors are typically comprised of a selectable marker that is either maintained in a replicon or developed into an integrating vector, as described above.

Expression and transformation vectors, either extrachromosomal replicons or integrating vectors, have been developed for transformation into many bacteria For example, expression vectors have been developed for, inter alia. the following bacteria: *Bacillus subtilis* [Palva et al. (1982) *Proc. Natl. Acad. Sci. USA* 79:5582; E.P.O. Pub. Nos. 36,259 and 63,953; P.C.T. WO 84/04541], *Escherichia coli* [Shimatake et al. (1981) *Nature* 292:128; Amann et al. (1985) *Gene* 40:183; Studier et al. (1986) *J. Mol. Biol.* 189:113; E.P.O. Pub. Nos. 36,776, 136,829 and 136,907; U.K. Patent Application Serial No. 8418273], *Streptococcus cremoris* [Powell et al. (1988) *Appl. Environ. Microbiol.* 54:655]; *Streptococcus lividans* [Powell et al. (1988) *Appl. Environ. Microbiol.* 54:655], *Streptomyces lividans* [U.S. Pat. No. 4,745,056].

Methods of introducing exogenous DNA into bacterial hosts are well-known in the art, and typically include either the transformation of bacteria treated with $CaCl_2$ or other agents, such as divalent cations and DMSO. DNA can also be introduced into bacterial cells by electroporation. Transformation procedures usually vary with the bacterial species to be transformed. See e.g., [Masson et al. (1989) *FEMS Microbiol. Lett.* 60:273; Palva et al. (1982) *Proc. Natl. Acad. Sci. USA* 79:5582; E.P.O. Pub. Nos. 36,259 and 63,953; P.C.T. WO 84/04541, Bacillus], [Miller et al. (1988) *Proc. Natl. Acad. Sci.* 85:856; Wang et al. (1990) *J. Bacteriol.* 172:949, Campylobacter], [Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids. In *Genetic Engineering: Proceedings of the International Symposium on Genetic Engineering* (eds. H. W. Boyer and S. Nicosia); Mandel et al (1970) *J. Mol. Biol.* 53:159; Taketo (1988) *Biochim. Biophys. Acta* 949:318; Escherichia], [Chassy et al. (1987) *FEMS Microbiol. Lett.* 44:173 Lactobacillus]; [Fiedler et al. (1988) *Anal. Biochem* 170:38, Pseudomonas]; Augustin et al. (1990) *FEMS Microbiol. Lett.* 66:203, Staphylococcus], [Barany et al. (1980) *J. Bacteriol.* 144:698; Harlander (1987) " Transformation of *Streptococcus lacts* by electroporation, in: *Streptococcal Genetics* (ed. J. Ferretti and R. Curtiss III); Perry et al. (1981) *Infec. Immun.* 32:1295; Powell et al. (1988) *Appl. Environ. Microbiol.* 54:655; Somkuti et al. (1987) *Proc. 4th Evr. Cong. Biotechnology* 1:412, Streptococcus].

Yeast Expression System

A yeast promoter is any DNA sequence capable of binding yeast RNA polymerase and initiating the downstream (3') transcription of a coding sequence (e.g. structural gene) into mRNA. A promoter will have a transcription initiation region which is usually placed proximal to the 5' end of the coding sequence. This transcription initiation region typically includes an RNA polymerase binding site (the "TATA Box" ) and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences Examples include alcohol dehydrogenase (ADH)(E.P.O. Pub. No. 284044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK)-(E.P.O. Pub No 329203) The yeast PH05 gene, encoding acid phosphatase, also provides useful promoter sequences [Myanohara et al ( 1983) *Proc. Natl. Acad Sci USA* 80:1].

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, OR PH05 genes, combined with the transcriptional activation region of a glycolytic enzyme gene such as GAP or PyK(E.P.O. Pub. No. 164556). Furthermore, a yeast promoter can include naturally occurring promoters of non-yeast origin that have the ability to bind yeast RNA polymerase and initiate transcription. Examples of such promoters include, inter alia, [Cohen et al. (1980) *Proc. Natl. Acad. Sci USA* 77:1078; Henikoff et al. (1981) *Nature* 283:835; Hollenberg et al. (1981) *Curr. Topics Microbiol. Immunol.* 96:119; Hollenberg et al (1979) "The Expression of Bacterial Antibiotic Resistance Genes in the Yeast Saccharomyces cerevisiae," in: *Plasmids of Medical, Environmental and Commercial Importance* (eds. K. N. Timmis and A. Puhler); Mercerau-Puiqalon et al. (1980) *Gene* 11:163; Panthier et al. (1980) *Curr. Genet.* 2:109;].

A DNA molecule may be expresser intracellularly in yeast A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative to direct expression. Typically, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See e.g., E.P.O. Pub. No. 196056. Another example is a ubiquitin fusion protein. Such a fusion protein is made with the ubiquitin region that preferably retains a site for a processing enzyme (e.g. ubiquitin-specific processing protease) to cleave the ubiquitin from the foreign protein. Through this method, therefore, native foreign protein can be isolated (P.C.T. WO 88/024066; commonly owned U.S. patent application Ser. No. 359,599, filed 7 August 1989, the disclosure of which is incorporated herein by reference). This system is the currently preferred system for producing IGFBP-6.

Alternatively, foreign proteins can also be secreted from the cell into the growth media by creating chimeric DNA. molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment typically encodes a signal peptide comprised of hydrophobic amino acids which direct the secretion of the protein from the cell.

DNA. encoding suitable signal sequences can be derived from genes for secreted yeast proteins, such as the yeast invertase gene (E.P.O. Pub. No. 12873; J.P.O. Pub. No. 62,096,086) and the A-factor gene (U.S. Pat. No. 4,588,684). Alternatively, leaders of non-yeast origin, such as an interferon leader, exist that also provide for secretion in yeast (E.P.O. Pub. No. 60057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders typically about 25 to about 50 amino acid residue:) (U.S. Pat. Nos. 4,546,083 and 4,870,008; E.P.O. Pub. No. 324274). Additional leaders employing an alpha-factor leader fragment that provides for secretion include hybrid alpha-factor leaders made with a presequence of a first yeast, but a pro-region from a second yeast alpha factor. (See e.g., P.C.T. WO 89/02463.)

Typically, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Typically, the above described components, comprising a promoter, leader (if desired), coding sequence of interest, and transcription termination sequence, are put together into expression constructs. Expression constructs are often maintained in a replicon, such as an extrachromosomal element (e.g., plasmids) capable of stable maintenance in a host, such as yeast or bacteria. The replicon may have two replication systems, thus allowing it to be maintained, for example, in yeast for expression and in a procaryotic host for cloning and amplification. Examples of such yeast-bacteria shuttle vectors include YEp24 [Botstein et al. (1979) *Gene* 8:17–24], pCl/1 [Brake et al. (1984) *Proc. Natl. Acad. Sci USA* 81:4642–4646], and YRp17 [Stinchcomb et al. (1982) *J. Mol. Biol.* 158:157]. In addition, a replicon may be either a high or low copy number plasmid. A high copy number plasmid will generally have a copy number ranging from about 5 to about 200, and typically about 10 to about 150. A host containing a high copy number plasmid will preferably have at least about 10, and more preferably at least about 20. Either a high or low copy number vector may be selected, depending upon the effect of the vector and the foreign protein on the host. See e.g., Brake et al., supra.

Alternatively, the expression constructs can be integrated into the yeast genome within an integrating vector. Integrating vectors typically contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver et al. (1983) *Methods in*

*Enzymol.* 101:228–245]. An integrating vector may be directed to a specific locus in yeast by selecting the appropriate homologous sequence for inclusion in the vector. See Orr-Weaver et al., supra. One or more expression construct may integrate, possibly affecting levels of recombinant protein produced [Rine et al. (1983) *Proc. Natl. Acad. Sci. USA* 80:6750]. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Typically, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions [Butt et al. (1987) *Microbiol. Rev.* 51:351].

Alternatively, some of the above described components can be put together into transformation vectors. Transformation vectors are typically comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: *Candida albicans* [Kurtz, et al. (1986) *Mol. Cell. Biol.* 6:142], *Candida maltosa* [Kunze, et al. 91985) *J. Basic Microbiol.* 25:141], *Hansenula polymorpha* [Gleeson, et al. (1986) *J. Gen. Microbiol.* 132:3459; Roggenkamp et al. (1986) *Mol. Gen. Genet.* 202:302], *Kluyveromyces fragilis* [Das, et al. (1984) *J. Bacteriol.* 158:1165], *Kluyeromyces lactis* [De Louvencourt et al. (1983) *J. Bacteriol.* 154:737; Van den Berg et al. (1990) *Bio/Technology* 8:135], *Pichia guillerimondii* [Kunze et al. (1985) *J. Basic Microbiol.* 25:141], *Pichia pastoris* [Cregg, et al. (1985) *Mol. Cell. Biol.* 5:3376; U.S. Pat. Nos. 4,837,148 and 4,929,555], *Saccharomyces cerevisiae* [Hinnen et al. (1978) *Proc. Natl. Acad. Sci. USA* 75:1929; Ito et al. (1983) *J. Bacteriol.* 153:163], *Schizosaccharomyces pombe* [Beach and Nurse (1981) *Nature* 300:706], and *Yarrowia lipolytica* [Davidow, et al. (1985) *Curr. Genet.* 10:380471 Gaillardin, et al. (1985) *Curr. Genet.* 10:49].

Methods of introducing exogenous DNA into yeast hosts are well-known in the art, and typically include either the transformation of spheroplasts or of intact yeast cells treated with alkali cations. Transformation procedures usually vary with the yeast species to be transformed. See e.g., [Kurtz et al. (1986) *Mol. Cell. Biol.* 6:142; Kunze et al. 91985) *J. Basic Microbiol.* 25:141; Candida]; [Gleeson et al. 91986) *J. Gen. Microbiol.* 132:3459; Roggenkamp et al. (1986) *Mol. Gen. Genet.* 202:302; Hansenula]; [Das et al. (1984) *J. Bacteriol.* 158:1165; De Louvencourt et al. (1983) J. Bacteriol. 154:1165; Van den Berg et al. (1990) *Bio/Technology* 8:135; Kluyveromyces]; [Cregg et al. (1985) *Mol. Cell. Biol.* 5:3376; Kunze et al. (1985) *J. Basic Microbiol.* 25:141; U.S. Pat. Nos. 4,837,148 and 4,929,555; Pichia]; [Hinnen et al. (1978) *Proc. Natl. Acad. Sci. USA* 75;1929; Ito et al. (1983) *J. Bacteriol.* 153:163 Saccharomyces]; [Beach and Nurse (1981) *Nature* 300:706; Schizosaccharomyces]; [Davidow et al. (1985) *Curr. Genet.* 10:39; Gaillardin et al. (1985) *Curr. Genet.* 10:49; Yarrowia].

Diagnostic Methods using Antigens

The compositions comprising antigens of the invention, as well as the genetic material, can be used in diagnostic assays. Among the biologically useful information that can be obtained is excessive binding protein levels due to the presence of tumors, that result in increased production of either IGF or one of the IGFBP binding proteins (since the binding proteins are produced in the presence of excess IGF). Additionally, a number of known disorders can be related to IGF concentrations. For example, some types of osteoporosis are related to IGF levels. Additionally, the binding proteins can be used in the identification, production, and purification of recombinantly produced IGFs. Methods for detecting the presence of IGFBP-6 comprise analyzing a biological sample such as a blood sample, cerebrospinal fluid, or tumor or bone tissue.

Typically, methods for detecting analytes such as binding proteins of the invention are based on immunoassays. Such techniques are well known and need not be described here in detail. Examples include both heterogeneous and homogeneous immunoassay techniques. Both techniques are based on the formation of an immunological complex between the binding protein and a corresponding specific antibody. Heterogeneous assays for IGFBP-6 typically use a specific monoclonal or polyclonal antibody bound to a solid surface. Sandwich assays are increasingly popular. Homogeneous assays, which are carried out in solution without the presence of a solid phase, can also be used, for example by determining the difference in enzyme activity brought on by binding of free antibody to an enzyme-antigen conjugate. A number of suitable assays are disclosed in U.S. Pat. Nos. 3,817,837, 4,006,360, 3,996,345.

The solid surface reagent in the above assay is prepared by known techniques for attaching protein material to solid support material, such as polymeric beads, dip sticks, or filter material. These attachment methods generally include non-specific adsorption of the protein to the support or covalent attachment of the protein, typically through a free amine group, to a chemically reactive group on the solid support, such as an activate carboxyl, hydroxyl, or aldehyde group.

In a second diagnostic configuration, known as a homogeneous assay, antibody binding to an analyte produces some change in the reaction medium which can be directly detected in the medium. Known general types of homogeneous assays proposed heretofore include (a) spin-labeled reporters, where antibody binding to the antigen is detected by a change in reported mobility (broadening of the spin splitting peaks), (b) fluorescent reporters, where binding is detected by a change in fluorescence efficiency, (c) enzyme reporters, where antibody binding effects enzyme/substrate interactions, and (d) liposome-bound reporters, where binding leads to liposome lysis and release of encapsulated reporter. The adaptation of these methods to the protein antigen of the present invention follows conventional methods for preparing homogeneous assay reagents.

Diagnostic Applications using Genetic Probes

The genetic material of the invention can itself be used in numerous assays as probes for genetic material present in naturally occurring materials. The analyte can be a nucleotide sequence which hybridizes with a probe comprising a sequence of (usually) at least about 16 consecutive nucleotides, usually 30 to 200 nucleotides, up to substantially the full sequence of the sequences shown above (cDNA sequences). The analyte can be RNA or cDNA. The sample is typically as described in the previous section. A positive result is generally characterized as identifying a genetic material comprising a sequence at least about 70% homologous to a sequence of at least 12 consecutive nucleotides of the sequences given herein, usually at least about 80% homologous to at least about 60 consecutive nucleotides within the sequences, and may comprise a sequence substantially homologous to the full-length sequences. In order to detect an analyte, where the analyte hybridizes to a probe, the probe may contain a detectable label. Probes that are particularly useful for detecting binding proteins are based on conserved regions of these proteins, particularly from amino acids 181–191 (PNCD) and amino acids 212–215 (CWCV) of IGFBP-6. These amino acids are highly conserved in all of the related IGF binding proteins. Only IGFBP-1 has a difference, a N for a D at position 191.

One method for amplification of target nucleic acids, for later analysis by hybridization assays, is known as the polymerase chain reaction or PCR technique. The PCR technique can be applied to detecting IGFBP-6 of the invention in suspected samples using oligonucleotide primers spaced apart from each other and based on the genetic sequence set forth herein. The primers are complementary to opposite strands of a double stranded DNA molecule and are typically separated by from about 50 to 450 nt or more (usually not more than 2000 nt). This method entails preparing the specific oligonucleotide primers and then repeated cycles of target DNA denaturation, primer binding, and extension with a DNA polymerase to obtain DNA fragments of the expected length based on the primer spacing. Extension products generated from one primer serve as additional target sequences for the other primer. The degree of amplification of a target sequence is controlled by the number of cycles that are performed and is theoretically calculated by the simple formula 2n where n is the number of cycles. Given that the average efficiency per cycle ranges from about 65% to 85%, 25 cycles produce from 0.3 to 4.8 million copies of the target sequence. The PCR method is described in a number of publications, including Saiki et al., Science (1985) 230:1350–1354; Saiki et al., Nature (1986) 324:163–166; and Scharf et U.S. Pat. Nos. 4,683,194; 4,683,195; and 4,683,202.

The invention includes a specific diagnostic method for determination of IGFBP-6, based on selective amplification of IGFBP-6-encoding DNA fragments. This method employs a pair of single-strand primers derived from non-homologous regions of opposite strands of a DNA. duplex fragment selected from the sequences set forth in FIG. 1. These "primer fragments," which form one aspect of the invention, are prepared from IGFBP-6 fragments such as described above. The method follows the process for amplifying selected nucleic acid sequences as disclosed in U.S. Pat. No. 4,683,202, as discussed above.

Monoclonal Antibodies

For both in vivo use of antibodies to IGFBP-6 and anti-idiotype antibodies and diagnostic use, it may be preferable to use monoclonal antibodies. Monoclonal anti-virus particle antibodies or anti-idiotype antibodies can be produced as follows. The spleen or lymphocytes from an immunized animal are removed and immortalized or used to prepare hybridomas by methods known to those skilled in the art. To produce a human-human hybridoma, a human lymphocyte donor is selected. Epstein-Barr virus (EBV) can be used to immortalize human lymphocytes or a human fusion partner can be used to produce human-human hybridomas. Primary in vitro immunization with peptides can also be used in the generation of human monoclonal antibodies. Antibodies secreted by the immortalized cells are screened to determine the clones that secrete antibodies of the desired specificity.

Assay for Biological Properties of IGFBP-6

The property of binding to an insulin-like growth factor is one of the biological activities of the proteins of the invention. These proteins may be conveniently tested in a binding assay using IGF-I Rinderknecht, E. and Humbel, R. E., J. Biol. Chem. (1978) 253 2769] or IGF-II [Rinderknecht, E. and Humbel, R. E., FEBS (1978) 89: 283], preferably IGF-II, in a labelled, e.g., iodinated, form. For example, such an assay may conveniently include performing a gel electrophoresis (SDS-PAGE) of the proteins of the invention, followed by a western blot of the gel, then incubating the blot in the presence of $^{125}$I]IGF-I or II, washing the blot to remove free IGF-I or -II, and detecting the radioactivity on the blot.

Sources of IGFBP-6

While IGF-BPs of the invention originally means human IGF-BPs, IGF-BPs of mammals, e.g. murine, procine, equine or bovine, are included within the definition of IGF-BPs as long as they comply with the required degree of homology.

The IGF-BPs of the invention include those purified from a tissue extract or from a conditioned culture medium as well as those obtained by recombinant means.

Uses of IGFBP-6

Therapeutic applications of the binding proteins of the invention include its use as a single therapeutic agent and its use in combination with an IGF, the latter use being preferred.

When used in combination with an IGF, a binding protein of the invention is suitable for use in the indications above mentioned, primarily as a growth inducing, tissue regenerating or wound healing agent.

Accordingly, the invention provides:

i) use of a binding protein of the invention together with IGF in free or fixed combination for stimulating the growth of a subject, tissue or organ regeneration or wound healing, or ii) a method of stimulating the growth of a subject, tissue or organ regeneration of wound healing in a subject which comprises administering a therapeutically effective amount of a binding protein of the invention together with a therapeutically effective amount of an IGF to a patient in need of such treatment, or iii) a pharmaceutical composition for stimulating the growth of a subject, tissue or organ regeneration or wound healing which comprises a binding protein of a invention together with an IGF and with a pharmaceutically acceptable carrier or diluent, or iv) a package containing separate until dose forms of a binding protein of the invention and an IGF, together with instructions for nixing or concomitant administration.

In association with an IGF, a binding protein of the invention is of special interest for mediating chondrogenesis or hematopoiesis. This may be shown in the following tests A to C.

A) An IGF increases bone formation as indicated by e.g. an increased incorporation of [3H]-proline into collagen and non-collagen proteins in fetal rat calvaria. A synergistic effect occurs when an IGF is used in the presence of a binding protein of the invention. Organ cultures of rat calvaria are prepared by dissecting frontal and parietal bones from 21-day old fetal rats, splitting along the sagittal suture and culturing according to the method of Kream et al. (Endocrinology (1985) 116. 296). A binding protein or IGF is added in doses from 10 to 200 ng/ml of cultures. When they are added to combination to each other the molar ratio is 1:1. Culturing is effected for 24 to 48 hours. To quantitate the incorporation of [3H]proline into collagenase-digestible protein and non-collagen protein, bone homogenates are digested with bacterial collagenase according to the method of Diegelman R. and Peterkofsky (Dev. Biol. (1972) 28:443) and modified by Kream et al. (Endocrinology (1985) 116:296).

B) An IGF decreases bone resorption as indicated by a decrease in release of [45]Ca from bone. A synergistic effect occurs when an IGF is used in the presence of a binding protein of the invention. The test is effected according to the principles of Raisz (J. Clin. Invest. (1965) 44:103). Pregnant rats are injected s.c. with [45]Ca on the eighteenth day of gestation. An IGF, alone or in the presence of a binding protein of the invention, is injected at a dose of 10 ng to 200 ng per animal. The binding protein is added so that the molar ratio of IGF is 1:1. On day nineteen, the animals are sacrificed, the fetuses removed. The mineralized shafts of the radii and ulnae are dissected and placed in culture. Resorption is quantitated on the basis of release of [45]Ca from the bone explants.

C) The IGF-binding proteins of the invention as well as other IGF-binding proteins potentiate the erythropoietin-like effect of IGF-I. This may be, in particular, demonstrated by testing IGF-I, e.g. 10 ng/ml IGF-I, alone and in combination with the mature IGF binding protein of FIG. 1, e.g. a 50 μl aliquot of a supernatant derived from a culture of a CHO cell line expressing the mature IGF binding protein of FIG. 1, in a CFU-E assay as described in Fagg, B. Roitsch, C. A. Cell, Physiol. (1986) 126:1. Whereas the result obtained with IGF-binding protein alone is not significantly different from the control, a synergistic effect of the combination is seen when compared to IGF-I alone.

Further, the mitogenic activity of an IGF combined with a binding protein of the invention may be tested as follows: The incorporation of [3H]methyl-thymidine into CCL 39 cells (Chinese hamster lung fibroblasts) in culture is measured as described by Plouet et al. Cell. Miol. (1984) 30:105. In this assay, cell line CCI 39 is seeded in a plate at 40 000 cells per well in 0.5 ml MEM culture medium (Gibco) containing 10% fetal calf serum 0.1% penicillin, 0.4% streptomcyin and 0.5% fungizone. After 72 hours incubation at 37° C. in an atmosphere loaded with 5% $CO_2$. Cells are washed with MEM medium in the absence of fetal calf serum and then cultured in this medium for 20 hours. At this stage, the cell culture is confluent and an IGF or a binding protein or both together are inoculated each at a dose of 10 ng to 200 ng culture medium. When added together the molar ratio must be 1:1. The test sample is incubated at 37° C. for 24 hours and then added with 1 μCi [3H]methylthymidine in 10 μl PBS. After 4 hours incubation the incorporation of methylthymidine is stopped by washing cells with PBS. Cells are fixed with 0.5 ml trichloroacetic acid (5%) for 30 min., washed with water and finally lysed with 0.5 ml of HaOH 0.1M for 2 hours at 37° C. 0.5 ml of lysate is transferred into a scintillation flask and mixed with 3 ml of scintillation liquid for measuring β-radioactivity. The binding protein potentiates the mitogenic activity of IGF although the radioactivity level that is measured when a binding protein is used alone is not substantially different from that of the control sample.

More particularly a binding protein of the invention, in combination with an IGF is useful a) for treating hypopituitarism. Laron-type dwarfism, osteoporosis, anemias especially complications following an chronic renal failure and liver or kidney deficiency and b) for promoting healing of wounds such as ulcers and burns or those occuring in accidental events or resulting from surgery.

For use in association with a binding protein of the invention, IGF is preferably selected from IGF-I as described in Rinderknecht, E. and Humbel, R. E., J. Biol. Chem. (1978) 253:2769. IGF-II as described in Rinderknecht, E. and Humbel, R. E., FEBS (1978) 89:283 and any derivative or fragment of IGF-I and IGF-II having an insulin-like growth factor activity. Most preferably, this is IGF-II.

For use in association with an IGF, a binding protein of the invention is preferably a protein which is from 85% to 100% homologous with pre IGF-BP or IGF-BP as shown in FIG. 1.

When not associated with IGFs, binding proteins of the invention have further therapeutic applications in any physiological disorders resulting from an excessive production of free IGFs, e.g. IGF-producing cancers such as breast or kidney cancer, diabetic proliferative retinopathy or a normal growth of tall children with high serum level of free IGF.

Accordingly, the invention also provides:

(i) the use of a binding protein of the invention for treating physiological disorders resulting from an excessive production of free IGF by a mammalian, for example human body, e.g. IGF-producing cancers, diabetic retinopthy or abnormal growth of tall subjects, or (ii) a method of treating physioligical disorders resulting from an excessive production of free IGF, e.g. IGF-producing cancers, diabetic retinopathy or abnormal growth of a subject which comprises administering a therapeutically effective amount of a binding protein of the invention to a subject in need of such treatment, or (iii) a pharmaceutical composition for treating physiological disorders resulting from an excessive production of free IGF, e.g. IGF-producing cancers, diabetic retinopathy or abnormal growth of a subject which comprises a binding protein of the invention in association with a pharaceutically acceptable carrier or diluent, or (iv) a method of delivering IGFs to specific organs or tissues based on the differential binding properties of IGFBP-6, as indicated by biological testing.

Fragments of mutated forms of the pre-IGF-BP or IGF-BP as shown in FIG. 1 are of particular value for treating the physiological disorders resulting from an excessive production of free IGF in the human body.

A binding protein of the invention, alone or in combination with an IGF, may be administered by any conventional route suitable for peptides, or particular enterally, e.g. in the form of tablets or capsules or, preferably parenterally, e.g. subcutaneously or intravenously in the form of injections of infusions. Further, it may be also used topically, e.g. in the form of ointments or suspensions when used, e.g. as a wound healing agent.

For all the above indications the appropriate dosage will of course vary depending upon, for example, the nature and severity of the disorder to be treated and the mode of administration. For example, satisfactory results may be obtained in the treatment of osteoporosis or anemia at daily dosages from about to 0.1 μg/kg to 40 μg/kg body weight, preferably from about 0.5 μg/kg to about 20 μg/kg body weight of a binding protein of the invention. In larger mammals, for example humans, as indicated daily dosage is from about 5 μg conveniently administered parenterally, for example once a day. For wound healing, a daily dose of from 0.1 to 10 μg of a protein of the invention per cm2 wound area is suitably indicated in larger mammals, for example humans. This is conveniently administered once a day. When used in combination with an IGF, the molar ratio of the binding protein to IGF is preferably from 0.1:1 to 5:1, more preferably from 0.5:1 to 2:1, most preferably 1:1.

Pharmaceutical compositions of the invention may be manufactured in conventional manner.

Other uses for the binding proteins of the invention include various uses in the production of IGF molecules by recombinant techniques. The binding proteins of the invention can be used to detect yeast-produced IGF in native (active) conformation (as opposed to inactivated forms). Additionally, the proteins of the invention can be used as carrier (possibly in the form of co-expressed proteins) in the production of IGF. As the binding protein stabilized IGF in vivo, they are expected to do the same in vitro. The binding proteins can also be used to purify IGF produced in yeast by attaching them to a solid surface (such as in affinity chromatography).

While the invention has been described with reference to particular embodiments, methods, construction, and use, it will be apparent to those skilled in the art that various changes and modifications can be made without departing from the invention.

EXAMPLE 1

Sepharose-IGF I affinity column

Sixty mg recombinant human IGF I (Ciba-Geigy AG, Basel, Switzerland) was dissolved in 20 ml 0.1M NaHCO$_3$, pH 8.3, containing 0.5M NaCl and coupled to CNBr-activated Sepharose 48 (4 g dry gel) according to the protocol of the supplier (Pharmacia Fine Chemicals, Uppsala, Sweden). The gel was equilibrated with 500 ml 0.05M sodium phosphate buffer/0.5M NaCl, pH 6.5, in a 1.5×15 cm glass column (gel bed volume 15 ml).

Purification of serum IGFBPs

This procedure was carried out according to a modification of the procedure of Martin and Baxter (1986) *J. Biol. Chem.* 261:8754–8760, and Zapf et al. (1988) *Biochem. Biophy. Res. Comm.* 156:1187–1194. One liter of out-dated human citrate plasma was stirred for 2 hours at room temperature with 50 U (1 ml) thrombin-calcium, filtered through cheesecloth and acidified. Dissociated IGF was removed with SP-Sephadex C-25. The pH was subsequently adjusted to 6.5 and the precipitate removed by centrifugation at 20,000 rpm for 30 min. The supernatant was pumped through the Sepharose-IGF I affinity column described above at 34 ml/min and the column washed with 500 ml 0.05M sodium phosphate buffer/0.5M NaCl, pH 6.5. Binding protein (i.e., IGFBP) was eluted with 40 ml 0.5M acetic acid, dialyzed 3 times against two liters of 0.1M ammonium acetate, and lyophilized. The lyophilized material (40 mg) was dissolved in 4 ml 0.1M heptafluorobutyric acid containing 20% (v/v) acetonitrile, and the insoluble material was removed by centrifugation at 10,000 for 10 min. The clear supernatant was subjected to HPLC (2 runs with 2 ml each) on a Nucleosil C$_{18}$ column (Macherey-Nagel, D ren, FRG), see Zapf et al. (1988) *Biochem. Biophys. Res. Comm.* 156:1187–1194. Effluent fractions were dried in a Speed-Vac (Savant Instruments, Hicksville, N.Y.), taken up in 1 ml 0.01M acetic acid, and dried again. The resulting material was dissolved in 250 μl H$_2$O for ligand blot analysis (see below) and silver staining, see Nilson et al. (1984) *Anal. Biochem.* 141:311–315.

$^{125}$I-IGF ligand blot analysis

The method of Hossenlopp et al. (1986) *Anal. Biochem.* 154:138–143 was used with slight modifications, see Zapf et al. (1989) *Proc. Natl. Acad. Sci. USA* 86:3813–3817, and Zapf et al. (1988) *Biochem. Biophy. Res. Comm.* 156:1187–1194. Five-μl aliquots of the HPLC effluent fractions were subjected to electrophoresis on 15% SDS polyacrylamide slab gels under non-reducing conditions. The $^{14}$C-labeled molecular weight marker (Rainbow Marker, Amersham, UK) was reduced. The gels were transblotted on nitrocellulose membranes and processed as described, in Hosselopp et al. (1986) *Anal. Biochem.* 154:138–143. Membranes were incubated for 6 h at room temperature in a sealed plastic bag with 3×10$^6$ cpm $^{125}$I-labeled IGF II, see Zapf et al. (1981) *J. Clin. Invest.* 68:1321–1330. After several washes the air-dried membranes were exposed for 12–48 h at −70° C. to an X-ray film (Kodak, X-OMAT TM, AR) in a Kodak X-OMATIC cassette (Eastman, Rochester, N.Y.).

$^{125}$I-IGF II was chosen as the tracer for screening because not all of the bands are detected with $^{125}$I-IGF I (see below).

Electroblotting on polyvinylidene difluoride (Immobilon) membrane

Ten to thirty μg of HPLC-purified IGFBP was electrophoresed as described above (polyacrylamide slab gels 15×15×0.15 cm) under reducing conditions and electroblotted (2 h at 0.8 A) on an Immobilon membrane (Millipore Corp., Bedford, Mass.) as described by Matsudaira, (1987) *J. Biol. Chem.* 262:10035–10038. The membrane was stained for 5 sec with 0.1% Coomassie Blue R-250 in 50% methanol, destained in 50% methanol/10% acetic acid for 5 min at room temperature, and then thoroughly rinsed in H$_2$O. The membrane was air-dried, and the protein bands were cut out and stored at −20° C.

Amino acid analysis was performed by automated Edman degradation using an Applied Biosystems Model 470A protein sequencer (Foster City, Calif.), see Hunkapiller et al. (1983) *Methods in Enzymology*, 91:399–413.

Tissue and RNA isolation

Human osteosarcoma tissue was obtained from Dr. Marshall Urist, UCLA. Total RNA was isolated by the guanidinium thiocyanate method, see Chirgwin et al. (1979) *Biochemistry* 18:5294–5299. An Osterizer was used to homogenize the tissue. Poly(A)+ RNA was purified by a single fractionation over oligo(dT) cellulose, see Aviv et al. (1972) *Proc. Natl. Acad. Sci. USA* 69:1408–1412.

Oligonucleotide synthesis

Oligonucleotide adaptors, probes, and sequencing and PCR primers were synthesized by the phosphoramidite method with an Applied Biosystems (Foster City, Calif.) model 380A synthesizer, purified by polyacrylamide gel electrophoresis, and desalted on SEP-PAK $C_{18}$ cartridges (Waters; Milford, Mass.).

A 14-mer oligonucleotide (5' CCTGTAGATCTCCG 3') and a 18-mer oligonucleotide (5' AATTCGGAGATCTACAGG 3') were synthesized and used as the EcoR1 adaptors for the human osteocarcinoma cDNA library constructed in λZAP. The 14-mer was phosphorylated, see Maniatis et al. (1982) "Molecular Cloning, a Laboratory Manual" (Cold Spring Harbor Lab, Cold Spring Harbor, N.Y.), then immediately heated to 95° C. for 15 min to inactivate the polynucleotide kinase. The adaptors also contain an internal Bgl II site and are described more fully in the following section describing the construction of the cDNA library.

The two PCR primers for IGFBP-6 were: (1) a "sense" primer consisting of a mixture of 64 27-mers [5' AGATCTGAATTCGCA(A/G)GGXGTX-CA(A/G)GC 3'] and (2) an "antisense" primer consisting of a mixture of 64 28-mers [5' AGATCTGAATTC-G(A/G)TC(C/T)TC(C/T)TC(C/T)TCXAC 3'] where X denotes all four deoxynucleotides. Eco RI sites were included in the primers to allow for subcloning into M13 sequencing vectors. The IGFBP-6 probe was a 23-mer [5' GCGGGTTGTCCAGGGGGCTGCGI 3'].

PCR amplification of IGFBP-6 sequences

The PCR reactions were performed according to the supplier of the PCR kit (Perkin/Elmer/Cetus) using the PCR primers described (see Oligonucleotide Synthesis section) at a final concentration of 8 μM. The template cDNA was synthesized from 2.5 μg of human osteosarcoma (Ost2) poly(A)+RNA The conditions of cDNA synthesis were identical to those described below for first strand cDNA synthesis (see Construction of cDNA Library). The cDNA was fractionated on Biogel A-15m, recovered by ethanol precipitation, and resuspended in 100 μl of sterile water. From 2.5 to 5 μl of cDNA template were used for each PCR reaction. Thirty-five cycles of PCR were performed in a Perkin-/Elmer/Cetus DNA thermocycler. The first 10 cycles consisted of a 94° C., 1 min. denaturation step; a 45° C., 1 min. annealing step; and a 45° C., 1 min. extension step. The next 25 cycles consisted of a 94° C., 1 min. denaturation step; a 55° C., 1 min. annealing step; and a 72° C., 1 min. extension step. The final extension step at the last cycle was 7 min. Samples were extracted once with phenol/chloroform/IAA (1:1:0.04), once with chloroform/IAA (24:1), recovered by ethanol precipitation, digested with EcoRI, and fractionated by electrophoresis on a 7% acrylamide, 1× TBE gel, see Maniatis et al., above. DNA migrating between 40–70 b.p. was excised from the gel, purified by passage over an Elutip-d column, ligated to Eco-RI cut m13 mo18, and introduced into DH5αF' for DNA sequencing.

Construction of the cDNA library

First-strand cDNA was synthesized from human osteosarcoma (Ost3) poly(A)+ RNA as described in Okayama et al. (1983) *Mol. and Cell. Biol.* 3:280–289, but with the following modifications: 10 μg of poly(A)+ RNA was heated to 65° C. for 3 min in 20 μl 5 mM Tris-hydrochloride (pH 7.5), immediately placed on ice for 1 min, and then adjusted (at room temperature) to contain 50 mM Tris-hydrochloride (pH 8.3 at 42° C.), 8 mM MgCl, 30 mM KCl, 10 mM dithiothreitol, 2 mM each of dATP, dGTP, dTTP and [$\alpha^{-32}$] dCTP (300 cpm/pmol), 60 U RNasin, and 2.5 μg of oligo (dT)12-18 Sixty μU of cloned Moloney Murine Leukemia Virus reverse transcriptase was added to initiate cDNA synthesis (total reaction volume 40 μl), and the reaction was continued for 60 min at 42° C. The second cDNA strand was synthesized and ligated to the EcoRl adaptors (see Oligonucleotide Synthesis section) as described in Aruffo et al. (1987) *Proc. Natl. Acad. Sci. USA* 84:8573–8577. The dscDNA was phosphocylated, see Maniatis et al, above and then adjusted to 0.5M NaCl/25 mM EDTA and heated at 75° C. for 15 min to inactivate the polynucleotide kinase. The dscDNA was separated from unligated adaptors by chromatography on Biogel A-15m and recovered by ethanol precipitation. The dscDNA was ligated to EcoRl-cut λZAP (Stratagene) as described by the supplier, but including 15% polyethylene glycol (PEG) 8000 (Sigma) in the reaction medium, a modification previously described in Pfieffer et al. (1983) *Nuc. Acids. Res.* 11:7853–7871. The ligated DNA was recovered by centrifugation (12,000×g), washed with chloroform, dried, resuspended in 4 μl $H_2O$, and incubated with an in vitro packaging extract (Stratagene) according to the supplier. A library of $2.3 \times 10^7$ independent recombinant clones was obtained. Recombinant phages were propagated in *E. coli* BB4 (Stratagene).

Screening of the cDNA library

Approximately 300,000 recombinant phages from the Ost3 cDNA library were plated 50,000 phages/137 mm dia. plate) in *E. coli* BB4 and grown for 5–6 hours at 37° C. The phages were transferred onto nitrocellulose filters (Millipore, HATF 137), processed, see Benton et al. (1977) *Science* 196:180, and screened with the IGFBP-6 probes. The IGFBP-6 probe was labeled with $T_4$ polynucleotide kinase and [$\gamma^{-32}p$] ATP (28) to a specific activity of $1-2 \times 10^8$ cpm/μg. The filters were prehybridized for 1–2 h at 37° C. in 5×SSC (1 SSC=0.15M sodium chloride/0.015M sodium citrate, pH 7) 40% formamide, 5×Denhardt's solution (1×Denhardt's solution=0.02% polyvinylpyrrolidone/0.02% Ficoll/0.02% bovine serum albumin), 10% dextran sulfate, 50 mM sodium phosphate, pH 6.8, 1 mM sodium pyrophosphate, 0.1% NaDodSO$_4$, and 50 μg/ml denatured salmon sperm DNA. Labeled probe was added to a concentration of $10^6$ cpm/ml, and hybridization was continued overnight at 37° C. with gentle shaking. The filters were washed in 2×SCC/0.1% NaDodSO₄ at 60° C. and exposed to Kodak XAR-2 films with a DuPont Lightning Plus intensifying screen overnight at −80° C. Areas of plaques giving duplicate signals were picked, replated, and rescreened until pure plaques were obtained.

Plasmid Isolation, Subcloning, and Sequencing

Bluescript SK(−) containing IGFB-6 cDNA inserts were released from λZAP by the M13 rescue/excision protocol described by the supplier (Stratagene). Plasmid DNA was isolated by the alkaline lysis method, see Maniatis et al., above. The inserts were excised from the Bluescript SK(−) vector by a Bql II digestion and fractionated by agarose gel electrophoresis. Inserts were excised from the gel and passively eluted for 12 h with gentle shaking in 10 mM Tris-hydrochloride pH 7.5, 1 mM EDTA. (TE), purified by elutip-D as described by supplier (Schleicher and Schuell), and subcloned into a M13 sequencing vector, see Yanisch-Perron et al. (1985) *Gene* 33:103–119. DNA sequencing was performed by the dideoxy chain termination method, see Sanger et al. (1977) *Proc. Natl. Acad. Sci. USA* 74:5463–5467 using M13 primers as well as specific internal primers. Ambiguous regions were resolved using 7-deaza-2-deoxyguanidinetriphosphate, see Barr et al. (1986) *Biotechniques* 4:428–432 and sequenase (US Biochemicals).

Deposit of Genetic Information

The genetic sequences set forth in FIG. 1 are on deposit with the American Type Culture Collection where they are identified as follows:

| Cloned Protein | Internal Identifier | In *E. coli* Strain | ATCC Number |
|---|---|---|---|
| IGFBP-6 | pBsBP4.1 | RR1 Δ M15 | 68388 |

We claim:

1. A recombinant DNA molecule comprising a cDNA encoding insulin-like-growth-factor binding protein (IGFBP-6) or a protein which is substantially the same.

2. A recombinant DNA molecule consisting essentially of an isolated nucleic acid encoding insulin-like-growth-factor binding protein (IGFBP-6), whose sequence is as set forth in FIG. 1.

3. The recombinant DNA molecule of claim 1, which comprises a human cDNA.

4. The recombinant DNA molecule of claim 2, which is a genomic DNA.

5. The recombinant DNA molecule of claim 1, wherein said molecule is pBsBP4.4.1.

6. A transformed microorganism or cell line containing the DNA molecule of claim 1.

7. The microorganism of claim 6, wherein said microorganism is a yeast.

8. The cell line of claim 6, wherein said cell line is a CHO cell line.

9. A method for producing insulin-like-growth-factor binding protein (IGFBP-6) or a protein which is substantially the same, said method comprising growing a recombinant host cell containing the DNA molecule of claim 1 under conditions wherein said IGFBP-6 is expressed by the host cell and then isolating the expressed IGFBP-6.

10. The method of claim 9, wherein said host cell is a microorganism.

11. The method of claim 9, wherein said host cell is a eucaryotic cell.

* * * * *